United States Patent [19]

Fons

[11] Patent Number: 5,281,024
[45] Date of Patent: Jan. 25, 1994

[54] METHOD FOR LOCATING POROUS AND PERMEABLE SOILS EMPLOYING EARTH SURFACE TEMPERATURE

[76] Inventor: Lloyd C. Fons, 14410 Cindywood Dr., Houston, Tex. 77079

[21] Appl. No.: 984,213

[22] Filed: Nov. 30, 1992

Related U.S. Application Data

[63] Continuation-in-part of Ser. No. 923,477, Aug. 3, 1992.

[51] Int. Cl.$^5$ .............................. G01N 25/00
[52] U.S. Cl. ........................ 374/45; 374/137; 73/38
[58] Field of Search ............ 73/38, 73, 75, 154; 374/136, 137, 45; 250/253

[56] References Cited

U.S. PATENT DOCUMENTS

| | | | |
|---|---|---|---|
| 3,847,351 | 11/1974 | Hasenbeck | 73/75 |
| 3,916,678 | 11/1975 | Lohoff | 73/73 |
| 4,332,172 | 6/1982 | Torstensson | 73/73 |
| 4,476,716 | 10/1984 | Fons | 73/154 |
| 4,561,290 | 12/1985 | Jewell | 73/38 |
| 4,612,802 | 9/1986 | Clarke et al. | 374/45 |
| 4,845,978 | 7/1989 | Whitford | 374/45 |

*Primary Examiner*—Robert J. Warden
*Assistant Examiner*—Hien Tran
*Attorney, Agent, or Firm*—Douglas H. May

[57] ABSTRACT

A method for locating surface deposits of porous, permeable soils having high percolation rates at locations having both permeable and impermeable soils present. During warmer periods of the year, when ambient atmospheric temperatures and soil temperatures are higher than the annual mean temperatures for the location, earth surface temperatures are measured at a plurality of points within a location. Points having relatively higher temperatures are identified as likely to have surface soils more porous and permeable than soils at points having relatively lower temperatures. The porosity and permeability of the soils at selected points may be quantified by testing the soil's percolation rates.

10 Claims, No Drawings

METHOD FOR LOCATING POROUS AND PERMEABLE SOILS EMPLOYING EARTH SURFACE TEMPERATURE

CROSS REFERENCE TO RELATED APPLICATIONS

This application is a continuation-in part of Fons' U.S. patent application Ser. No. 07/923,477, filed Aug. 3, 1992, entitled "Methods For Locating Oil Or Gas Deposits Employing Earth Surface Temperatures, now pending

BACKGROUND OF THE INVENTION

1. Field of the Invention

The present invention relates to methods for locating porous, permeable soils having high percolation rates, such as sands or gravels, at locations having both permeable and impermeable soils present. Particularly, the present invention relates to methods for locating porous, permeable soils by measuring the temperature of the earth's surface at a number of points within the bounds of a selected location, then, comparing the measured temperatures to identify those points having earth surface temperatures higher than those at other points within the location. Soils beneath points having higher temperatures tend to be more porous and permeable and to have higher percolation rates than soils beneath points having lower temperatures.

The ability to identify and locate porous and permeable soils is useful in environmental matters which involve land drainage patterns. Porous, permeable soils with higher percolation rates drain water faster than more impermeable soils. One particular use for the method of the present invention is to locate surface deposits of porous, permeable soils which are suitable for use as evaporation fields for septic tank systems.

2. Description of Pertinent Art

In U.S. Pat. No. 4,476,716, I disclosed methods for predicting the likelihood that oil or gas deposits are present below selected locations. These methods were based upon the discovery that earth temperatures tend to be lower at locations where oil or gas deposits exist than earth temperatures at the same depth at locations where oil or gas deposits do not exist.

In U.S. patent application Ser. No. 07/923,477, filed Aug. 3, 1992 and copending with this application, I disclosed methods for predicting whether oil or gas deposits are likely to be present beneath selected locations, which methods employ differences in the temperature of the earths surface from point to point. These methods for locating oil or gas deposits are based upon the discovery that earth surface temperatures above oil or gas deposits are slightly, but measurably, less than the average earth surface temperature for the surrounding area.

In developing these methods for finding oil or gas deposits, I observed that the earth's surface and near surface temperatures are affected by a wide variety of environmental factors, including: seasonal temperature fluctuations; diurnal effects; fluctuations in incident radiation; ambient atmospheric temperature; atmospheric humidity; wind velocity; cloud cover; atmospheric clarity; precipitation; reflectance and emmissivity of the earth's surface; vegetative cover; surface elevation above sea level; local topography; surface features; and, pertinent to the present invention, soil moisture and soil type. The effect of all these factors taken together tends to obscure the effect of any one factor, and my inventions have involved methods for extracting meaningful information from earth temperature measurement data.

The present invention arose from observing workers at homesites on Washington Island, Wis. The workers were attempting to locate soils having sufficient porosity and permeability to serve as evaporation fields for septic tank systems. Washington Island is comprised of thin soils overlying Silurian limestone. Many of the soils are relatively impermeable silts and clays in which water tends to pool. Interspersed in these impermeable soils are sand and gravel beds, such as remnants of ancient beaches, which are porous and permeable, have high water percolation rates and are suitable for septic tank evaporation field sites. At each homesite, the workers were digging, with tractor mounted back-hoes, to locate sand and gravel beds suitable for septic tank evaporation fields. The digging process was slow, destroyed vegetation, and created unnecessary holes at each homesite. From these observations of the workmen's efforts, it became apparent that an improved method for locating the porous, permeable sand and gravel beds was desirable.

Septic tank systems treat sewage, generally from a single family or other small source. Such septic tank systems comprise:

- a septic tank where sewage is received for digestion by anaerobic bacteria and for production of waste water;
- a drain line for transporting waste water from the septic tank; field lines for receiving waste water from the drain line; and
- an evaporation field comprised of porous, permeable material, such as sand or gravel, where waste water received from the field lines is evaporated.

Waste water from a septic tank is evaporated in the evaporation field, and should never be allowed to drain away, either into surface waters or into subsurface aquifers. Consequently, surface deposits of porous, permeable materials having high percolation rates are selected as sites for septic tank evaporation fields. Preferably, the surface deposits are underlain by more impermeable deposits which prevent water from percolating downward into subsurface aquifers.

Sands and gravels have the desired porosity, permeability and high water percolation rates which make such deposits suitable for septic tank evaporation fields. Air, as well as water, circulates through the porous and permeable sand and gravel beds, increasing the rate of evaporation. Heavier soils, such as silt and clay, are fine grained and have little porosity or permeability. Air cannot circulate in such heavy soils, and water is held in them by capillary action. Consequently evaporation rates from silt and clay soils are low, and such soils are not suitable for use in septic tank evaporation fields.

SUMMARY OF THE INVENTION

Now, according to the present invention, I have discovered an improved method for locating porous, permeable soils at locations having both porous, permeable soils and impermeable soils, which method comprises:
  selecting a location likely to have both porous, permeable soils and impermeable soils present;
  selecting a time period when ambient temperatures and soil surface temperatures are above the mean annual atmospheric temperature for the location, and when the soil is neither frozen nor water logged;

measuring, during the selected time period, earth surface temperatures at a plurality of points within the bounds of the location; selecting points with earth surface temperatures higher than earth surface temperatures at other points within the location, as being located in areas with higher permeability then areas around points with lower temperatures.

DETAILED DESCRIPTION AND PREFERRED EMBODIMENTS OF THE INVENTION

The surface and near surface of the earth are affected by seasonal fluctuations in atmospheric temperature. At the near surface depth to which the affects of seasonal temperature variations reach, in many cases the temperature is constant at about the value of the mean annual atmospheric temperature. From this near surface limit, the temperature of the earth begins its steady temperature increase proportional to depth. From that limit to the surface, the temperature of the earth fluctuates in response to temperature effects at the surface. Considering the mean annual temperature, and the depth to which seasonal temperature changes reach, it is apparent that heat flows downward from the earths surface in the warmer seasons, and then upward toward the surface in cooler seasons.

Porous and permeable soils which have high percolation rates, such as sand and gravel beds, do not hold moisture well and contain air in the interstices between the grains of sand or gravel. The air, as well as water, circulates through such porous, permeable soils which increases the rate of evaporation from such soils. The heavier clay and silt soils, which are more impermeable and have small pores compared to sand and gravel, hold moisture by capillary action and contain little air. Consequently, evaporation rates from these more impermeable soils is low. Earth surfaces above porous and permeable soils are warmer than earth surfaces above more impermeable soils, such as silts and clays. While not wishing to be bound by any theory of why temperatures vertically above such porous, permeable soils tend to be higher than temperatures above impermeable soils, consideration of the wide differences in thermal conductivity between air and water indicates that permeable porous soils, which contain substantial volumes of air, may be considerably less thermally conductive than are more impermeable soils which contain little air, but contain substantial amounts of water. Thus, according to this view, during the warmer months when heat flows downward from the earth's surface, the earth's surface temperature above porous, permeable sand and gravel deposits would tend to be higher than temperatures above more impermeable soils, such as silts and clays. That is, heat will be carried downward and away from the surface more rapidly over the more impermeable soils due to such soils having higher heat capacities than the porous, permeable sands and gravels.

According to the present invention, earth surface temperatures may be measured remotely, as with an infra-red sensor, or directly in physical contact with the earth using a temperature measuring device, such as a thermometer or thermistor. When an infra-red sensor is employed to measure earth surface temperatures, the sensor is desirably maintained at about the same elevation above and at about a 90° angle to the earth's surface at each point to minimize the effect of variations in thickness of intervening atmosphere upon the measured temperatures. Preferably, the sensor will be in sufficiently close proximity to the earth's surface that moisture and haze in the intervening atmosphere will not have a substantial effect upon the temperature measurements obtained. Most preferably, the sensor will be within about one to four feet above and at substantially a 90° angle to the earth's surface where the temperature is being measured.

When temperature measuring devices in direct contact with the earth are used, preferably the temperature is measured at the at the actual earth surface. These positions for the temperature measuring devices give the most accurate and repeatable temperature measurements. The accuracy and repeatability of the measurements made becomes less as the deviation from the preferred positions increases.

From the depth at which the temperature is constant to the surface, the earth's temperature fluctuates with seasonal temperature changes, while at the surface, the earth's temperature is also affected by a variety of factors, including: diurnal effects, fluctuations in incident radiation, ambient temperature, atmospheric humidity, wind velocity, cloud cover, atmospheric clarity, precipitation, reflectance and emissivity of the earth's surface, vegetative cover, elevation, local topographical and surface features, and soil moisture and soil type. Additionally, earth surface temperatures are effected by subsurface conditions such as, for example, presence or absence of oil or gas deposits, as described in copending application U.S. Ser. No. 07/923,477. Consequently, the near-surface temperature of the earth varies throughout the year to the depth at which the annual temperature fluctuations reach. The temperature of the earth at the depth to which the temperature fluctuations reach is, in many cases about constant at the value of the mean annual atmospheric temperature for the location under consideration.

According to methods of the present invention, earth surface temperature measurements are made at a plurality of points within the bounds of a selected location within a short time period when temperature fluctuations and variations due to seasonal, diurnal, ambient and topographical conditions are minimized and the temperature differences arising from the differences in soils porosities and permeabilities can be measured directly. This method is particularly adapted for use at locations where very little or no subsurface control is available, and available data may contain unrepresentative numbers of points likely to have the porous, permeable soils being sought beneath them.

A location for application of the present method will generally be about the size of a homesite. That is, a location will preferably have an area not larger than several acres. If an area to be surveyed using the present method is larger than several acres, then the area may be more effectively surveyed by breaking it into two or more locations and surveying each location separately. The location selected must be large enough to contain beds of the porous, permeable soils being sought, and beds of less porous soils, such that earth surface temperatures may be obtained and distinguished at points above each type of soil. Generally locations selected for application of the methods of the present invention are sufficiently small that subsurface features will not create temperature anomalies within the bounds of the individual locations.

Occasionally, however, temperature anomalies due to the subsurface features will appear within the bounds of an individual location. In such cases the bounds of the location must be adjusted to remove such subsurface effects. For example, a location may be divided into two, one having all of the subsurface higher temperature anomaly, and the other having all of the subsurface lower temperature anomaly. Reducing the effect of these extraneous factors upon the measured earth surface temperatures aids in discerning the small earth surface temperature differences arising from variation in porosity and permeability of soils within the bounds of a single location.

A point, as used herein, is a single spot on the earth's surface selected for measuring the earth's surface temperature. According to the present invention, soils beneath points having earth surface temperatures higher than earth surface temperatures at other points within the same location are likely to be more permeable and porous than the soils beneath the points having lower earth surface temperatures. Consequently, a plurality of points are selected within a location of interest, sufficient in number to locate and delineate the boundaries of surface deposits of the porous, permeable soils of interest. Preferably, selected points within the bounds of a location of interest have similar topographical, vegetative cover and surface features for minimizing the effect of extraneous features upon the temperatures measured.

Surface features encompass many types of features which affect the earth's surface temperature, and these features generally vary substantially from point to point. Desirably, points having similar surface features are selected for reducing the effect of surface features upon the variance in measured earth surface temperatures. After elimination of points with gross differences in surface features, points for measurement of earth surface temperatures are selected for similarity of surface features by visual inspection, which is sufficient. Surface features to consider include: elevation, slope, pooled water or saturated soil, surface reflectance and emissivity, vegetative cover, as well as other topographical features.

Environmental factors such as ambient temperature, diurnal effects, local climatic effects, soil moisture content, atmospheric moisture content, precipitation, rate of moisture evaporation, wind velocity, incident radiation (sunlight or the lack thereof), and other weather conditions are subject to rapid change and can substantially effect the earth surface temperatures. Consequently, the effect of these environmental factors is minimized by measuring earth surface temperatures at the selected points within selected, relatively short time periods within which the environmental factors will remain fairly constant. Preferably, earth surface temperatures at all points within a location are measured within a single, short time period of about 12 hours or less during which environmental factors will change little. The time periods will preferably be of several hours duration during each day when changes in environmental factors are minimum. Incident radiation (sunlight) has a very significant effect upon earth surface temperatures. Also, radiation of heat from the earth, particularly at night, has a significant effect upon earth surface temperatures. Consequently, earth surface temperatures are preferably measured when rates of incident radiation striking the earth and radiation leaving the earth are at a minimum, or are about equal over the area of study. A preferred time period for measuring earth surface temperatures is from about midnight, after most of the day's heat has radiated away, to before dawn, before incident radiation begins to increase for the new day. Cloudy conditions with little or no precipitation are preferred because cloud cover reduces both incident radiation striking the earth, and radiation leaving the earth.

Earth surface temperatures may be measured with any instrument which provides sufficient precision and reproducibility, including instruments which physically contact the earth's surface, as well as remote sensing instruments. Temperature measurements are preferably made to a precision of about $\frac{1}{4}°$ F., (about 1/10° C.), or less. Temperature differences of as little as $\frac{1}{4}°$ F. will in many cases be significant in finding and delineating beds of porous, permeable soils at selected locations.

Reproducibility of measured temperatures is also important. Preferably, instruments employed in measuring the earth surface temperatures will have no substantial drift such that the instruments reproduce substantially the same measured temperature value for repeated measurements at the same point. In the event instruments do drift, such that repeated temperature measurements do not provide the same value, it is preferable that the rate of such drift be determined and that the measured temperatures be corrected for drift before being used in the method of the present invention.

Examples of temperature measuring instruments which may be brought into physical contact with the earth to produce the desired temperature measurements include mercury thermometers, alcohol thermometers, bimetallic thermometers, thermistors, and thermocouples.

Examples of remote sensing instruments which may be used to obtain the desired temperature measurements include infra-red sensors. Preferably, the infra-red sensors will be tuned to have heightened sensitivity to radiation at wavelengths generated by objects having temperature in the range of the earth temperatures expected to be measured. Use of remote sensing infra-red instruments is preferred in the method of the present invention. Temperatures can be measured rapidly to a good precision with such instruments, any drift, or lack of repeatability, in temperature readings made with such infra-red sensors can generally be eliminated or compensated for by using a good quality sensor and following the manufacturer's operating instructions.

When earth surface temperatures are measured using remote sensing instruments, such as infra-red sensors, it is preferable that the sensors be maintained substantially the same distance above, and at an angle of about 90° to the earth's surface at each selected point where a temperature is measured. Maintaining the height and attitude of the sensor constant minimizes the effect of atmospheric conditions upon the values of measured temperatures. Atmospheric conditions, especially relative humidity, moisture fog, haze and so on may have substantial effects upon the values obtained for temperatures measured with remote sensing instruments. Effect of the atmospheric conditions upon measured values of temperature increases as the thickness of the atmosphere through which the measurement is made increases. Therefore, it is preferable that such sensors be maintained in close proximity to the earth surface at the selected points where the measurements are made. Distances above the surface of about one to four feet are preferable for ground based sensors, although greater or lesser distances can be used if conditions warrant.

EXAMPLES

The process of the present invention is illustrated by the following examples, which are given by way of illustration only, and not as limitations on the scope of this invention which is defined in the appended claims.

EXAMPLE I

This example illustrates the effect of intervening atmosphere upon earth surface temperature measurements obtained using a remote sensing infra-red instrument.

The infra-red sensing instrument employed in this example was a Omega Engineering Company Model OS82-LT infra-red thermometer, sensitive to radiation in the range of 8-14 microns, suitable for measuring earth surface temperatures to a precision of about 0.1° C.

In a first test, earth surface temperatures were measured remotely from a position about 90 feet above the earth surface. The test was made in the early evening on a day in mid-June at Tulsa Okla. For a first reading, the infra-red sensor was aimed stright down at an angle of 90° to the earths surface and the temperature measured. Then, for a second reading, the infra-red sensor was aimed at a point on the surface about 200 feet away where a earth surface temperature was measured. The atmosphere was hazy when the first test was made.

A second test was made from the same balcony the day after the first test was made. The second test was similar to the first test except: the second test was made in early morning, rather than in the evening; and the atmosphere was foggy rather than hazy.

Results of Tests 1 and 2 are shown in Table I, following.

TABLE I

| | TEST 1 | | TEST 2 | | |
|---|---|---|---|---|---|
| Time of day | 8:40 P.M. | | 7:00 A.M. | | |
| Atmospheric conditions | Hazy | | Foggy | | |
| Incident angle, sensor to surface | 90° | 66° | 90 | 66° | 1° |
| Distance, sensor to surface, feet | 90 | 219 | 90 | 219 | horizon |
| Measured temperatures, °F. | 88 | 80 | 78 | 74 | 63 |

The measured temperatures reported in Table I for Tests 1 & 2 indicate that temperatures measured with an infra-red sensor decrease as the distance between the sensor and the earth's surface increases. The atmosphere affects temperature measurements made with infra-red sensors. As shown in Test 1, the measured temperature of the earth's surface drops 8° F. (from 88° to 80°) as the thickness of the atmosphere intervening between the sensor and the earth's surface increases from 90 feet to 219 feet. Likewise, in Test 2 the earth surface temperature at the horizon measured 15° F. less than the earth surface temperature only 90 feet away from the sensor, The temperatures of the earth's surface and of the atmosphere seldom have the same value, and the infrared sensor measures radiation from both the earth's surface and from the intervening atmosphere. Thus, the temperature measured by the remote sensing infra red instrument is a composite of the temperatures of the intervening atmosphere and of the earth's surface. As the distance between the sensor and the earth's surface increases and, consequently the thickness of the atmosphere between the sensor and the earth's surface increases, the effect of the atmosphere on the measured temperature increases. Preferably then, the infra-red sensor is maintained at an angle of 90° and at a constant height above the surface being measured for maintaining the precision and repeatability of the temperature measurements. Further, the distance between the sensor and the surface being measured is preferably minimized, with a distance of one to four feet being particularly preferred.

EXAMPLE II

In this example, the method of the present invention was applied to a tract of land for demonstrating that porous, permeable beds of sand and gravel can be located employing these methods. A beach front tract on Washington Island, Wis. was selected as a location for study. The tract was forested except for the present beach area near the water. The beach area is bare and is composed of limestone cobbles. Soils on the tract are mainly relatively impermeable silty clays. Beds of sand and gravel, in the form of ancient beach ridges, run through these more impermeable soils. The sand and gravel beds are porous and permeable, and water evaporates readily from them. Thus, the sand and gravel beds deposited in the ancient beach ridges are suitable for use as evaporation fields for septic tank waste water.

The ancient beaches, and the benches upon which they lie, are sometimes, but not always, discernible as low rises extending generally parallel to present day beaches on the Island. Locating the ancient beaches by sight is often difficult, and sometimes impossible, especially in areas covered with woods. The ancient beaches, once found, are not entirely composed of the porous and permeable sand and gravel beds. Significant portions of the ancient beaches are composed of more impermeable materials which are not suitable for use as septic tank evaporation fields. Thus, the purpose of the experiments reported here was to employ the methods of the present invention to locate and delineate porous, permeable sand and gravel beds among the more impermeable soils on the location under study.

According to the present invention, the earth's surface above porous, permeable soils is predicted to be slightly warmer than the earth's surface above more impermeable soils. This prediction was tested in these Examples by making a number of traverses across the selected location measuring the earth's surface temperatures at a plurality of points in each traverse. Each traverse was from the inland boundary of the tract to the head of the present day beach. Earth surface temperatures were measured at about 2½ foot intervals using a hand-held infra-red sensor maintained at about three feet above the earth surface. The infra-red sensor used in all the experiments of this example was an Omega Engineering Company model OS82-LT Infrared thermometer, sensitive to infra-red radiation in the range of 8-14 microns, suitable for measuring earth surface temperatures to a precision of about 0.1° C.

A single traverse of the tract was made on an evening in mid June, at about 8:00 P.M. Rain had fallen earlier in the day, and the sky was overcast. The entire traverse was across wooded ground from the inland boundary of the location toward the beach. For a distance of about 700 feet, the earth surface temperatures were constant at 60° F. Then, the temperatures abruptly increased to 61° F. and remained at 61° F. for about 30 feet, then abruptly fell-back again to 60° F. for the final distance of about 75 feet to the head of the present day beach. The section of the tract with earth surface temperatures of 61° F. was, by visual observation, determined to be on the main ancient beach ridge present at the location.

From about 10:00-11:00 A.M. on the day after the first traverse was made, six additional traverses, similar in every way to the original traverse, were made across the location. Earth surface temperatures were measured at about 2½ foot intervals along the course of each traverse. Each traverse was spaced from the next by about 20 feet.

On the first traverse, earth surface temperatures at points along the traverse were in the range of 60°-61° F. from 0 to 700 feet; 62° F. from 700 to 730 feet, and 60°-61° F. from 730 to 800 feet.

On the second traverse, earth surface temperatures at points along the traverse were in the range of 60°-61° F. from 0 to 690 feet; 62°-63° F. from 690 to 720 feet; and 60°-61° F. from 720 to 800 feet.

On the third traverse, earth surface temperatures at points along the traverse were in the range of 60°-61° F. from 0 to 680 feet; 62°-63° F. from 680 to 710 feet; and 60°-61° F. from 710 to 800 feet.

On the fourth traverse, earth surface temperatures at points along the traverse were in the range of 60°-61° F. from 0 to 675 feet; 62°-63° F. from 675 to 705 feet; and 60°-61° F. from 705 to 800 feet.

On the fifth and sixth traverses, earth surface temperatures were in the range of 60°-61° F. over the entire length of each traverse.

Examination of the temperature measurements obtained, shows that for traverses 1-4, areas having higher earth surface temperatures (62°-63° F.) are bounded on both sides by areas having lower temperatures (60°-61° F.). According to the teaching of the present invention, the areas having higher earth surface temperatures are predicted to have greater porosity and permeability than adjacent areas having the lower (60°-61° F.) earth surface temperatures. The predictions of the present invention were confirmed by testing points along each of the traverses 1-4. A stake was driven at several points having lower (60°-61° F.) earth surface temperatures. In each case the soil was found to be either heavy silty clay or solid rock, both having low porosity and permeability. In further tests, the stake was driven at points having higher (62°-63° F.) earth surface temperatures. At these points of higher temperature, the stake was easily driven into unconsolidated beds of sand and gravel which were porous and permeable. The area of higher temperature, upon visual examination, appeared to comprise portions of the main ancient beach.

These areas of higher earth surface temperature (62°-63° F.) comprising beds of unconsolidated sand and gravel appear suitable for use as evaporation fields for septic tank systems. The areas of lower earth surface temperatures (60°-61° F.) comprising heavy silty clays and solid rock having low porosity and being relatively impermeable, are unsuitable for use as such evaporation fields.

For traverses 5 and 6, the earth surface temperatures were all in the range of 60°-61° F., and it appears that the porous, permeable sand and gravel beds of the ancient beach do not extend into the area covered by traverses 5 and 6. So, this area is not suitable for use as the site for evaporation fields.

While the invention has been described with reference to preferred embodiments, the same are to be considered illustrative only and not limiting in character, and that many changes and modifications may be made by those skilled in the art without departing from the spirit and scope of the invention which is defined only by the appended claims.

I claim:

1. A method employing measurements of earth surface temperatures for determining porous, permeable soils suitable for septic tank drainage fields within a location on the earth's surface comprising areas containing beds of porous, permeable soils and areas containing beds of less porous soils, which method comprises:
   a) selecting a location;
   b) selecting a plurality of points on the earth's surface within the location;
   c) selecting a time period, when ambient temperatures are greater than mean annual atmospheric temperatures for the location, and when soils within the location are neither frozen nor waterlogged;
   d) measuring, during the selected time period, earth surface temperatures at each of the plurality of points;
   e) determining points of the plurality of points having earth surface temperatures higher than earth surface temperatures at other points of the plurality of points;

wherein beds of soil within areas below the points of the plurality of points having earth surface temperatures higher than earth surface temperatures at other points of the plurality of points are likely to be more permeable and porous than beds of soil within areas below the other points of the plurality of points.

2. The method of claim 1, including:
   selecting, as members of the plurality of points, points having similar topographical, vegetative cover, and surface features; and
   selecting, as the time period, a time period during warmer months of the year when heat is flowing downward from the earth's surface within the location.

3. The method of claim 2, including:
   selecting a time period having substantially constant environmental factors.

4. The method of claim 1, including:
   a) determining an average temperature value of the earth surface temperatures measured at the plurality of points;
   b) determining points, of the plurality of points, having measured earth surface temperatures higher than the average earth surface temperature value;
   c) determining points, from the plurality of points, having measured earth surface temperatures at or below the average earth surface temperature value;
   wherein the points of the plurality of points having measured earth surface temperatures higher than the average earth surface temperature value are likely to be above areas having beds of soil more porous and permeable than beds of soil in areas below points of the plurality of points having measured earth surface temperatures at or below the average earth surface temperature value.

5. The method of claim 1, including:
   determining a percolation rate for soils in areas below the points of the plurality of points having measured earth surface temperatures higher than earth surface temperatures of other points of the plurality of points, for confirming the presence of beds of porous, permeable soils suitable for use as septic tank evaporation fields.

6. The method of claim 1, wherein the earth surface temperature measurements at each of the plurality of points are made with temperature measuring instruments in direct contact with the earth's surface.

7. The method of claim 1, wherein the earth surface temperature measurements at each of the plurality of points are made with a remote temperature sensing instrument.

8. The method of claim 7, wherein the remote temperature sensing instrument is an infra-red radiation sensing instrument.

9. The method of claim 8, wherein the infra-red sensing instrument is maintained at about a constant elevation above and at an angle of about 90 degrees to the earth's surface at points of the plurality of points where earth surface temperature measurements are being made.

10. The method of claim 9 wherein the infra-red sensing instrument is maintained at an elevation of about one to four feet above the earth's surface.

* * * * *